United States Patent
Subramanian

(10) Patent No.: US 11,511,087 B2
(45) Date of Patent: Nov. 29, 2022

(54) DUAL DOUBLE BALLOON CATHETER

(71) Applicant: BEST MEDICAL INTERNATIONAL, INC., Springfield, VA (US)

(72) Inventor: Manny R. Subramanian, Frederick, MD (US)

(73) Assignee: Best Medical International, Inc., Springfield, VA (US)

( * ) Notice: Subject to any disclaimer, the term of this patent is extended or adjusted under 35 U.S.C. 154(b) by 149 days.

(21) Appl. No.: 16/781,068

(22) Filed: Feb. 4, 2020

(65) Prior Publication Data
US 2020/0171285 A1     Jun. 4, 2020

Related U.S. Application Data

(60) Division of application No. 15/293,342, filed on Oct. 14, 2016, now Pat. No. 10,589,071, which is a
(Continued)

(51) Int. Cl.
*A61M 25/10*     (2013.01)
*A61M 5/00*      (2006.01)
(Continued)

(52) U.S. Cl.
CPC ..... *A61M 25/1011* (2013.01); *A61K 51/1282* (2013.01); *A61L 29/02* (2013.01);
(Continued)

(58) Field of Classification Search
CPC .............. A61M 25/1011; A61M 5/007; A61M 37/0069; A61M 2025/1047;
(Continued)

(56) References Cited

U.S. PATENT DOCUMENTS 2,799,273 A    7/1957   Oddo
4,976,266 A   12/1990   Huffman et al.
(Continued)

FOREIGN PATENT DOCUMENTS

| JP | 2009232882 | 10/2009 |
|----|------------|---------|
| WO | 99/27985   | 6/1999  |
| WO | 2008124149 | 10/2008 |
| WO | 2013049827 | 4/2013  |

OTHER PUBLICATIONS

U.S. Appl. No. 16/801,325, filed Feb. 26, 2020, Manny R. Subramanian.
(Continued)

*Primary Examiner* — Sunita Reddy

(57) ABSTRACT

A dual double balloon catheter includes a catheter having a proximal end portion, a central portion and a distal end portion, and a secondary treatment balloon for a catheter. The catheter includes a plurality of lumens within the catheter extending from the proximal end portion, a plurality of inflatable balloons positioned in the central portion and a secondary treatment balloon communicatively associated with the distal end portion of the catheter, and the balloons and the secondary treatment balloon being communicatively connected with a corresponding one of the plurality of lumens to selectively inflate/deflate the corresponding inflatable balloon or to receive a radioactive dose or a therapeutic agent for a treatment.

19 Claims, 6 Drawing Sheets

Related U.S. Application Data continuation-in-part of application No. 15/189,396, filed on Jun. 22, 2016, now Pat. No. 10,406,381, which is a continuation of application No. 12/889,032, filed on Sep. 23, 2010, now Pat. No. 9,402,980.

(60) Provisional application No. 62/242,976, filed on Oct. 16, 2015.

(51) Int. Cl.

| | | |
|---|---|---|
| *A61N 5/10* | (2006.01) | |
| *A61K 51/12* | (2006.01) | |
| *A61L 29/02* | (2006.01) | |
| *A61L 29/06* | (2006.01) | |
| *A61L 29/16* | (2006.01) | |
| *A61M 25/00* | (2006.01) | |

(52) U.S. Cl.
CPC ............. *A61L 29/06* (2013.01); *A61L 29/16* (2013.01); *A61M 5/007* (2013.01); *A61M 25/0017* (2013.01); *A61N 5/1002* (2013.01); *A61N 5/1007* (2013.01); *A61N 5/1015* (2013.01); *A61L 2300/102* (2013.01); *A61M 2210/1067* (2013.01); *A61M 2210/1089* (2013.01); *A61N 5/1016* (2013.01); *A61N 5/1071* (2013.01); *A61N 2005/1003* (2013.01); *A61N 2005/1004* (2013.01); *A61N 2005/1018* (2013.01); *A61N 2005/1021* (2013.01); *A61N 2005/1024* (2013.01); *A61N 2005/1025* (2013.01)

(58) Field of Classification Search
CPC ...... A61M 2025/1079; A61M 25/0017; A61M 2210/1067; A61M 2210/1089; A61M 25/10181; A61N 5/1007; A61N 5/1015; A61N 5/1016; A61N 2005/1003; A61N 2005/1004; A61N 2005/1024; A61N 2005/1025; A61N 2005/1018; A61N 2005/1021; A61N 5/1071; A61N 5/1002; A61K 51/1282; A61L 29/02; A61L 29/06; A61L 29/16; A61L 2300/102
USPC .......................................... 600/1, 3; 604/328
See application file for complete search history.

(56) References Cited

U.S. PATENT DOCUMENTS

| | | | |
|---|---|---|---|
| 5,623,940 A | 4/1997 | Daikuzono | |
| 5,653,683 A | 8/1997 | D'Andrea | |
| 5,720,717 A | 2/1998 | D'Andrea | |
| 5,782,800 A | 7/1998 | Yoon | |
| 5,913,813 A | 6/1999 | Williams et al. | |
| 6,119,697 A | 9/2000 | Engel et al. | |
| 6,165,199 A | 12/2000 | Barbut | |
| 6,251,059 B1 | 6/2001 | Apple et al. | |
| 6,258,019 B1 * | 7/2001 | Verin ................... | A61M 25/10 600/1 |
| 6,398,708 B1 * | 6/2002 | Hastings ............ | A61M 25/0127 600/3 |
| 6,398,709 B1 * | 6/2002 | Ehr ...................... | A61N 5/1002 600/3 |
| 6,447,462 B1 | 9/2002 | Wallace et al. | |
| 6,616,629 B1 | 9/2003 | Verin et al. | |
| 6,923,754 B2 | 8/2005 | Lubock | |
| 6,955,641 B2 | 10/2005 | Lubock | |
| 6,958,052 B1 | 10/2005 | Charlton | |
| 7,184,827 B1 | 2/2007 | Edwards | |
| 7,357,770 B1 | 4/2008 | Cutrer et al. | |
| 7,662,082 B2 | 2/2010 | White et al. | |
| 8,251,884 B2 | 8/2012 | Lubock et al. | |
| 8,277,370 B2 | 10/2012 | Quick | |
| 8,287,442 B2 | 10/2012 | Quick | |
| 8,348,825 B2 | 1/2013 | Partridge et al. | |
| 8,360,950 B2 | 1/2013 | Acosta et al. | |
| 8,568,284 B2 | 10/2013 | White et al. | |
| 8,961,383 B2 | 2/2015 | Parsai et al. | |
| 9,283,402 B2 | 3/2016 | Cutrer | |
| 9,402,980 B2 | 8/2016 | Subramanian | |
| 9,498,644 B2 | 11/2016 | Cutrer | |
| 9,895,253 B2 | 2/2018 | Giap et al. | |
| 10,406,381 B2 | 9/2019 | Subramanian | |
| 2003/0032851 A1 | 2/2003 | Apple et al. | |
| 2004/0087827 A1 | 5/2004 | Lubock | |
| 2005/0027157 A1 | 2/2005 | Winkler et al. | |
| 2005/0080313 A1 | 4/2005 | Stewart et al. | |
| 2005/0101824 A1 | 5/2005 | Stubbs | |
| 2005/0182286 A1 | 8/2005 | Lubock | |
| 2006/0100475 A1 | 5/2006 | White et al. | |
| 2006/0173233 A1 | 8/2006 | Lovoi | |
| 2006/0212002 A1 | 9/2006 | Fangrow, Jr. | |
| 2006/0212022 A1 | 9/2006 | Gellman | |
| 2007/0106108 A1 | 5/2007 | Hermann et al. | |
| 2007/0142695 A1 * | 6/2007 | White .................. | A61N 5/1015 600/7 |
| 2007/0167666 A1 | 7/2007 | Lubock et al. | |
| 2008/0215031 A1 | 9/2008 | Belfort et al. | |
| 2008/0221384 A1 | 9/2008 | Chi Sing et al. | |
| 2008/0281143 A1 * | 11/2008 | Lubock ................ | A61N 5/1002 600/3 |
| 2009/0082609 A1 | 3/2009 | Condado | |
| 2009/0143634 A1 | 6/2009 | Benson et al. | |
| 2009/0156880 A1 * | 6/2009 | Allan ................... | A61N 5/1015 600/3 |
| 2009/0198095 A1 | 8/2009 | Acosta et al. | |
| 2009/0209805 A1 | 8/2009 | Lubock et al. | |
| 2009/0254064 A1 | 10/2009 | Boatman | |
| 2009/0264696 A1 | 10/2009 | White et al. | |
| 2009/0306453 A1 * | 12/2009 | Popowski ............ | A61N 5/1015 600/7 |
| 2009/0312593 A1 | 12/2009 | Drobnik et al. | |
| 2009/0318855 A1 | 12/2009 | Ehrenreich | |
| 2010/0069878 A1 | 3/2010 | Parsi et al. | |
| 2010/0191034 A1 | 7/2010 | Cutrer et al. | |
| 2010/0204688 A1 | 8/2010 | Hoey et al. | |
| 2010/0331601 A1 | 12/2010 | Partridge et al. | |
| 2011/0034976 A1 | 2/2011 | Mon et al. | |
| 2011/0152683 A1 | 6/2011 | Gerrans et al. | |
| 2011/0230700 A1 * | 9/2011 | Sing .................... | A61N 5/1015 600/7 |
| 2012/0022314 A1 | 1/2012 | Sing et al. | |
| 2012/0172651 A1 * | 7/2012 | Cutrer ................. | A61N 5/1015 600/4 |
| 2012/0253099 A1 | 10/2012 | Mon et al. | |
| 2013/0030411 A1 | 1/2013 | Kreck | |
| 2014/0005539 A1 * | 1/2014 | Forster ................ | A61N 5/1007 600/431 |
| 2014/0066896 A1 | 3/2014 | Tilson et al. | |
| 2014/0257092 A1 | 9/2014 | Lamoureux et al. | |
| 2014/0275712 A1 | 9/2014 | D'Andrea | |
| 2014/0277466 A1 | 9/2014 | Teisen et al. | |
| 2016/0045212 A1 | 2/2016 | Janardhan et al. | |
| 2017/0028174 A1 | 2/2017 | Subramanian | |
| 2017/0035997 A1 | 2/2017 | Subramanian | |
| 2017/0333075 A1 | 11/2017 | Bacino et al. | |
| 2019/0053935 A1 | 2/2019 | Giap et al. | |
| 2019/0117519 A1 | 4/2019 | Schmid-Schonbein | |
| 2020/0171284 A1 | 1/2020 | Subramanian | |
| 2020/0171285 A1 | 2/2020 | Subramanian | |
| 2020/0197672 A1 | 6/2020 | Subramanian | |
| 2020/0306511 A1 | 6/2020 | Subramanian | |
| 2020/0338321 A1 | 10/2020 | Subramanian | |

OTHER PUBLICATIONS

U.S. Appl. No. 16/900,273, filed Jun. 12, 2020, Manny R. Subramanian.
U.S. Appl. No. 16/924,947, filed Jul. 9, 2020, Manny R. Subramanian.
Astro 2015 Annual Meeting, Ancer Medical, Hialeah, FL Booth 489, Print Profile, Oct. 2015, 2 pages.

(56) References Cited

OTHER PUBLICATIONS

Gilad N. Cohen et al., "Design of a Novel Applicator for Esophageal High Dose Rate Brachytherapy", Abstract PO51, Abstracts / Brachytherapy, vol. 14, 2015, pp. S101-S102.
"Whal is Esophageal Brachytherapy" Ancer Medical, Available at: http://www.ancermedical.com/wp-conlenl/ uploads/2016/04/Esophageal-Applicalor.pdf, 2016, 6 pages.
Esophageal Applicator (E-AppTM), Ancer Medical, 2016, 1 page.
Anorectal Applicator (AR) TM, Ancer Medical, 2016, 2 pages.
Esophageal Applicator (E-App)TM, Ancer Medical, Available at: http://www.ancermedical.com/wp-conlenl/ uploads/2016/04/Esophageal-Applicalor.pdf, 2016, 5 pages.
"Hologic takes SenoRx assets in out-of-court settlement with C.R. Bard", A. Sarvestani, www.massdevice.com, Aug. 14, 2013 {downloaded,Oct. 19, 2015), 4 pages.
"Best Dual Balloon Breast Brachytherapy Applicator", from TeamBest brochure/material, Sep. 13, 2014, 3 pages.
U.S. Appl. No. 12/889,032, filed Sep. 23, 2010, Subramanian.
U.S. Appl. No. 15/189,396, filed Jun. 22, 2016, Subramanian.
U.S. Appl. No. 15/292,923, filed Oct. 13, 2016, Subramanian.
U.S. Appl. No. 15/293,342, filed Oct. 14, 2016, Subramanian.
U.S. Appl. No. 62/242,976, filed Oct. 16, 2015, Subramanian.
U.S. Appl. No. 62/242,972, filed Oct. 16, 2015, Subramanian.
U.S. Appl. No. 16/775,629, filed Jan. 29, 2020, Manny R. Subramanian.

* cited by examiner

DUAL DOUBLE BALLOON CATHETER

CROSS-REFERENCE TO RELATED APPLICATIONS

This application claims priority under 35 U.S.C. § 120 to and is a divisional application of U.S. patent application Ser. No. 15/293,342, filed on, Oct. 14, 2016, which is a continuation-in-part (CIP) of U.S. patent application Ser. No. 15/189,396, filed on, Jun. 22, 2016, now issued as U.S. Pat. No. 10,406,381, which is a continuation application of U.S. patent application Ser. No. 12/889,032, filed on Sep. 23, 2010, now issued as U.S. Pat. No. 9,402,980, and U.S. patent application Ser. No. 15/293,342 also claims priority under 35 U.S.C. § 119 to U.S. Provisional Patent Application No. 62/242,976, filed on Oct. 16, 2015, all of which are hereby incorporated herein by reference in their entirety.

FIELD OF THE INVENTION

The invention generally relates to the field of medical devices, and more particularly to a dual double balloon catheter for delivering a radiation dose to a patient, measuring the inter images of internal organs and removing human waste while providing an easy connection module.

BACKGROUND

In medicine, a catheter is a device that can be inserted into a body cavity, duct, or vessel, such as a blood vessel. This process of inserting a catheter can be referred to as a catheterization. When a catheter is left inside the body of a patient, either temporarily or permanently, this can be referred to as an indwelling catheter. Further, a permanently inserted catheter can be referred to as a "Permcath".

By being adapted for insertion, catheters can allow for the drainage or injection of fluids. Additionally, catheters can also allow for access within a patient for surgical instruments, among other functions. In most uses, a catheter is a thin, flexible tube, which can be referred to as a "soft" catheter. In other uses, a catheter can be a larger, solid or "hard" catheter.

Incidence of esophageal and stomach cancers continue to increase globally. Often these cancer patients die without proper diagnosis and/or treatment. For localized cancers, tumors can be first shrunk with the help of a high dose rate brachytherapy device employing appropriate applicators. This can be followed by surgical, chemotherapeutic and/or biological agents for mediated targeted therapeutic procedures. The positioning and targeting of a radiation dose to a site of disease with minimal and/or no damage to normal nearby tissue can be a challenge. Therefore, it is desirable to have a catheter that can provide multiple functions and can also be positioned and targeted for delivering the radiation dose to a specific area of the patient, such as a stomach area, the prostrate and the uterus, among other examples.

Thus, a dual balloon catheter addressing the aforementioned problems is desired.

SUMMARY OF INVENTION

A dual double balloon catheter or multiple function balloon catheter includes a catheter having a proximal end portion, a central portion and a distal end portion. The catheter further includes a plurality of lumens within the catheter, and the central portion and/or the distal end portion has a plurality of spaced apart balloons thereon as can position and/or stabilize the catheters for treatment. The plurality of balloons can have varying sizes in relation to each other and also include lumens within or associated with the inner walls. These lumens of the balloons in the central portion and/or distal end portion can respectively contain radioactive wires or other therapeutic agents or treatment mediums for treatment of a patient or can contain an inflation medium, such as fluid mediums, such as a liquid, air or other gaseous medium, to selectively inflate and deflate the corresponding balloons. The dual double balloon catheter further includes an extraction point or an extraction opening that can remove fluids or material from a cavity, such as from an area adjacent to the cavity in the patient, and a marker placed at the tip of the catheter. The cavity for a treatment can include an esophagus, the rectum, the vagina or a surgically created cavity of a patient, for example. The plurality of inflatable balloons is also desirably configured to be positioned spaced from each other in a longitudinal direction along the length of the catheter. Also, the plurality of lumens are desirably associated with a multi-balloon inflator having a plurality of connectors or connector portions respectively associated with each of the lumens to selectively inflate or deflate one or more of the plurality of inflatable balloons independently of at least one other of the plurality of inflatable balloons, such as by an inflation medium, and to enable selectively providing a treatment medium or a contrast medium, such as a radioactive medium or therapeutic agent, to a corresponding balloon independently of at least one other inflatable balloon for a treatment, the plurality of connectors being configured to enable respectively selectively receiving or removing through corresponding ones of the plurality of lumens one or more of a liquid saline solution, a fluid medium, a gaseous medium, a contrast medium, a radioactive material or other treatment medium for a treatment. Also, the dual double balloon catheter desirably can be configured to deliver or provide a radiation treatment to the esophageal and stomach areas, such as areas having abnormal growth, while simultaneously removing fluid and material, such as tissue, from a cavity for a treatment, for example.

The catheter can also include a secondary treatment balloon positioned at the distal end portion and communicatively connected to one or more of the plurality of lumens, and at least one of the plurality of lumens is adapted to provide a medium to selectively inflate and deflate the secondary treatment balloon to selectively position and/or stabilize the secondary treatment balloon for delivery of the treatment and another of the plurality of lumens adapted to deliver a radioactive dose or a therapeutic agent for the treatment.

These and other features of the present invention will become readily apparent upon further review of the following specification and drawings.

DESCRIPTION OF THE DRAWINGS

Unless otherwise indicated, similar reference characters denote corresponding features consistently throughout the attached drawings.

DETAILED DESCRIPTION

The present disclosure relates to a dual double balloon catheter for delivering radiation, and for targeting single to multiple disease and organ sites with a dual balloon configuration. Additionally, the dual balloon catheter enables a fixing or positioning of radioactive wires in an esophagus and stomach area and other organs to deliver radiation to targeted portions of a patient. The dual balloon catheter can have a plurality of lumens for inserting radioactive wires or other therapeutic agents for treatment at the site or sites of the patient's tissue. For this purpose, the dual-purpose balloon catheter of the present invention can include at least one and desirably two or more lumens having a spiral configuration around one or more of the balloons therein extending to the distal end portion of the dual double balloon catheter. The dual double balloon catheter can additionally include a secondary treatment balloon having a spiral lumen adapted to receive a radioactive wire or other therapeutic agent at the distal position to treat tissue at the distal position of the catheter.

Figure 1A:
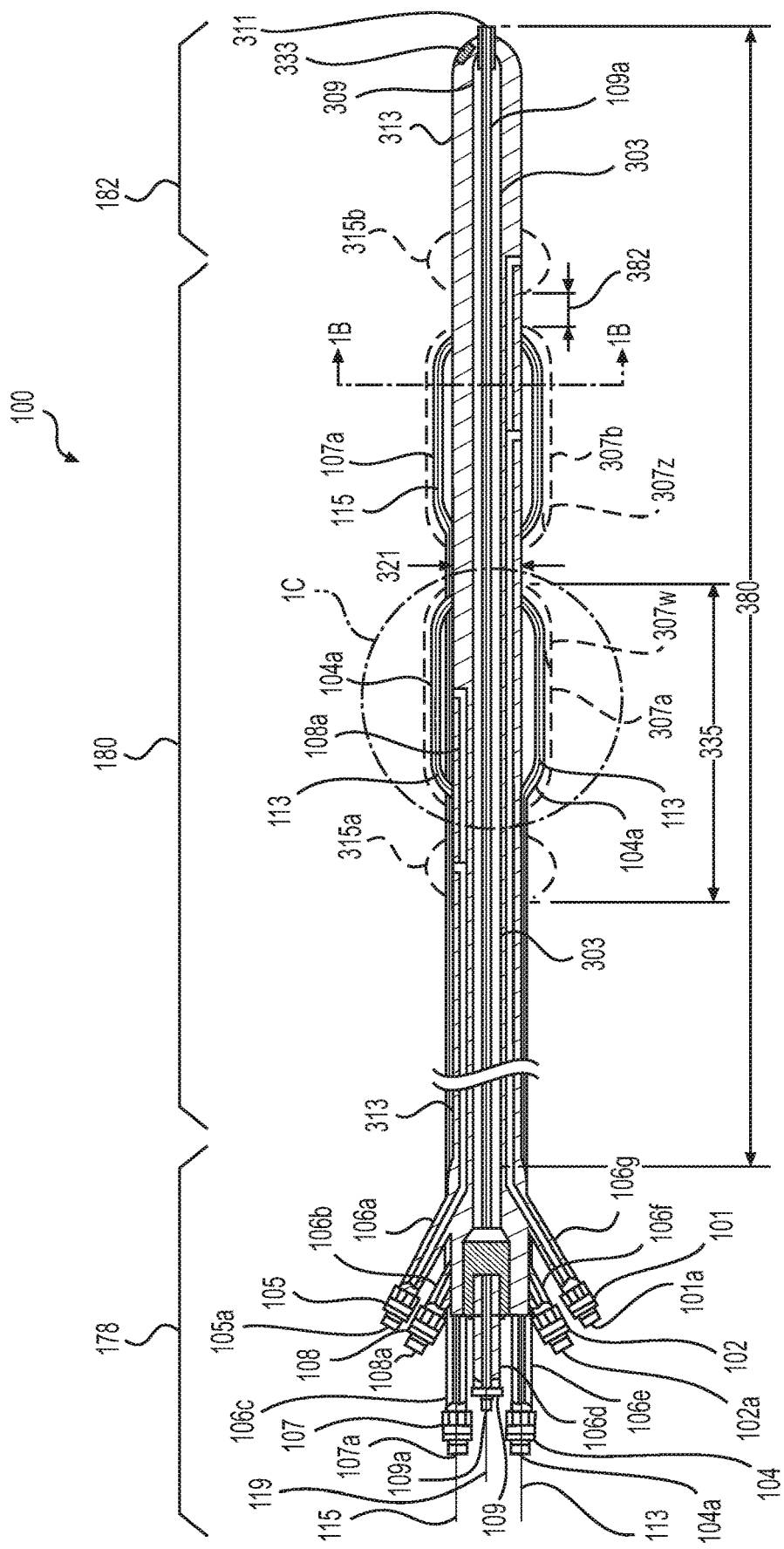
FIG. 1A is a longitudinal plan view of an embodiment of a dual double balloon catheter according to the present invention.

Referring now to the drawings in greater detail, there is illustrated in FIG. 1A an exemplary dual double balloon catheter 100 constructed according to the teachings of the invention. As illustrated in FIG. 1A, the double balloon catheter 100 includes a proximal end portion 178, a central portion 180, and a distal end portion 182. The proximal end portion 178 includes a plurality of connectors or connecting mechanisms, such as luer-lock connections, shown as luer-lock connections 101, 102, 104, 105, 107, 108 and 109.

Continuing with reference to FIG. 1A, the dual double balloon catheter 100 has the central portion 180 having a tubular body 313, for example, and the distal end portion 182. The distal end portion 182 can include a marker 333 that can assist in locating the dual double balloon catheter 100, and more specifically, locating the distal end portion 182, when an image, such as an x-ray, is taken of the patient.

The distal end portion 182 can also include a tip 311 that can provide or include an extraction opening and can be used for drawing human fluid material such as urine, pus, blood, from a cavity receiving a treatment, among other examples. The tip 311 can include or provide in association with the extraction opening of the tip 311 an inner seal that allows for a single direction of flow for removal of fluid or material from the cavity.

The dual double balloon catheter 100 is designed for multiple uses and features, for example, to deliver radiation to the esophageal and stomach areas having abnormal growth while simultaneously removing material, such as human fluid liquid, e.g., blood, urine, fat and tissue, from a cavity for treatment, if desired. Also, the dual double balloon catheter 100 has a plurality of connectors, such as male or female luer-lock connections 101, 102, 104, 105, 107, 108 and 109. In greater detail, the luer-lock connection 101 has a lumen 101a associated with a neck portion 106g of the catheter 100. The luer-lock connection 102 has a lumen 102a associated with a neck portion 106f of the catheter 100. The luer-lock connection 104 has a lumen 104a associated with a neck portion 106e of the catheter 100 and a radioactive wire 113 as can be inserted inside the lumen 104a for radiation treatment. The luer-lock connection 109 has a central lumen 109a associated with a neck portion 106d of the catheter 100 and can include a radioactive wire 119 as can be inserted inside the lumen 109a for radiation treatment. The luer-lock connection 107 has a lumen 107a and can include a radioactive wire 115 inside it as can be inserted inside the lumen 107a for radiation treatment and is associated with a neck portion 106c of the dual double balloon catheter 100. The luer-lock connection 108 has a lumen 108a associated with a neck portion 106b of the catheter 100. The luer-lock connection 105 has a lumen 105a associated with a neck portion 106a of the catheter.

The dual double balloon catheter 100 also has a central main lumen 303, with the central main lumen 303 running from a proximal end of the luer-lock connection 109 to the tip 311. The central main lumen 303 can extend through the dual double balloon catheter 100 to a secondary treatment balloon positioned at the tip 311 at the distal end portion 182 of the catheter 100. Now with attention directed to the lumens 101a, 102a, 104a, 105a, 107a, 108a, and 109a, the lumen 101a is communicatively connected to a balloon 307b for inflating the balloon 307b to a predetermined size so as to position and/or stabilize the dual double balloon catheter 100. The lumen 102a is connected to a balloon 315b for inflating balloon 315b to a desired size for positioning and/or stabilizing the dual double balloon catheter 100 in a cavity for a treatment. The lumen 105a is connected to a balloon 315a for inflating balloon 315a to a desired size, and the lumen 108a is communicatively connected to a balloon 307a for inflating balloon 307a to a desired size for positioning and/or stabilizing the dual double balloon catheter 100 in a cavity for a treatment.

As shown for the balloon 307a, the radioactive treatment wire 113 can run inside the lumen 104a, which is integrally formed along or suitably attached to an inner wall 307w of the positioning and/or stabilizing balloon 307a. In an embodiment, the lumen 104a can accommodate radioactive fluid instead of a radioactive wire or other therapeutic agent for a treatment. Typically, a length 380 of the dual double balloon catheter 100 of FIG. 1A is about 78 centimeters (cm) to the tip 311 from a proximal base portion such as including the central portion 180, as indicated in FIG. 1A. However, the length 380 can be any suitable length depending on the use or application of the dual double balloon catheter 100 and is not to be construed in a limiting sense.

Further, a diameter 321 of the dual double balloon catheter 100 of FIG. 1A is typically about 0.45 cm. However, the diameter 321 can be of any suitable value depending on the use of the dual double balloon catheter 100 and is not to be construed in a limiting sense. The typical diameter of the lumens 101a, 102a, 105a and 108a for inflating the balloons 307a, 307b, 315a, and 315b, are in the range of 0.8 mm to 1.5 mm, for example. However, the diameter of the lumens 101a, 102a, 105a and 108a can be any suitable size depending on the use of the dual double balloon catheter 100 and is not to be construed in a limiting sense. The balloons, such as the balloons 307b and 315b, can be positioned to be spaced apart from each other as indicated at 382 by a desired amount of by about 2.5 cm from each other. However, the spacing can be any suitable length depending on the use and application of the dual double balloon catheter 100 and is not to be construed in a limiting sense.

In embodiments, the dual double balloon catheter 100 can be made of various suitable materials such as of a polymeric material such as polyurethane, polyethylene, polymethyl methacrylate (PMMA), polycarbonate, styrenic block copolymers, polybutylene terephthalate (PBT), Teflon, Nylon or PVC, among other examples. The balloons, such as the balloons 307a, 307b, 315a, and 315b, can be made of nylon, polyurethane, Polyether block amide Pebax®, poly(ethylene terephthalate), commonly abbreviated PET or other thermoplastic elastomers, for example. Alternatively, the balloons 307a, 307b, 315a, and 315b can be uncoated or coated with a lubricant for lubrication or for antimicrobial properties. As another alternative, various therapeutic drugs can be coated onto the surface of the balloons, such as balloons 307a, 307b, 315a, and 315b, and/or coated on a surface of the catheter, for releasing a drug or other therapeutic agent, internally to a specific location of a cavity of the patient for treatment.

The dual double balloon catheter 100 of FIG. 1A has a plurality of luer-lock connections 101, 102, 104, 105, 107, 108 and 109, and a plurality of balloons, such as the balloons 307a, 307b, 315a, and 315b, which can be inserted into various body cavities. Examples of body cavities include the esophagus and the stomach area, but the body cavities are not limited thereto and could be inserted into any orifice such as the rectum, the vagina and a surgically created cavity for treatment. When the dual double balloon catheter 100 is used in conjunction with a patient for treatment, radioactive wires 113, 115, and 119, can provide the needed radiation dose to treat a cancerous growth within the patient. Typically, a dimension of the radioactive wires 113, 115, and 119, can be in a range of about 0.5 to 0.8 millimeters (mm), for example, but can depend on the particular use or application.

Desirably, the radioactive wires 113, 115, and 119 can be made of Iridium-192, Cobalt-60 and Yttrium-168, among other examples of suitable materials, as can depend on the use or application. A high dose rate (HDR) treatment application can be conducted with Ir-192, Au-198, I-125 and Cs-131, for example. Typically, the dose of radiation delivered is in a range of from about 1 Curie to about 10 Curies per seed. Various suitable HDR after-loaders can be used for treatment in conjunction with embodiments of catheters, such as the dual double balloon catheter 100, such as with various suitable commercially available after-loaders as, for example, Varisource, Gamma Med and BEBIG, among other examples. For a low dose rate (LDR) delivered by embodiments of a catheter, such as the catheter 100, Sr-90 can be used, as well as Cs-131 and Yb-168, for the radiation source. Typically, the dose of radiation using the LDR configuration is usually on an order of about one thousand times less, i.e., in a range of about 1 milli Curie to about 10 milli Curies, for example.

An advantage of the dual double balloon catheter 100 is that it can allow for delivery of a radiation dose or other treatment agent to a specific bodily site of the patient, while at the same time or at different times removing any fluid etc., from the site of the treatment. By allowing each balloon, such as balloons 307a, 307b, 315a, and 315b, to have such an independent connection, as described, such independent connection can advantageously enable medical personnel to selectively control the size of each balloon independently to adjust the location and for positioning and/or stabilizing the catheter, such as the catheter 100, at the treatment site. Moreover, the balloons, such as balloons 307a, 307b, 315a, and 315b, are configured in different sizes to allow for relatively better control and positioning in the body cavity for treatment. Further, the dual double balloon catheter 100 can advantageously enable delivering the radiation or other therapeutic agent along the sides of the dual double balloon catheter 100, such as for an esophagus area of the body cavity.

Figure 1B:
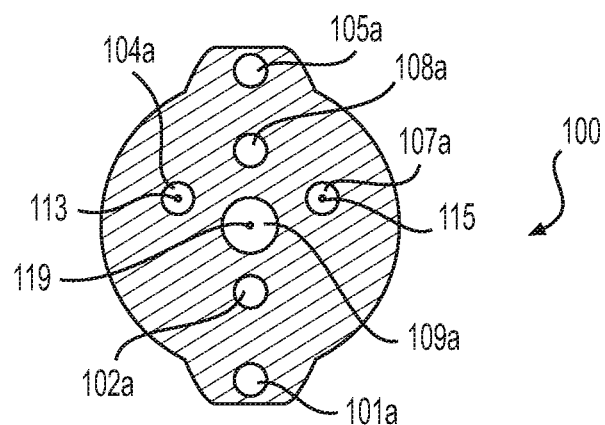
FIG. 1B is a cross-sectional view taken along the 1B-1B plane of the dual double balloon catheter of FIG. 1A according to the present invention.

Referring now to FIG. 1B, FIG. 1B shows a cross sectional view along the 1B-1B plane of the dual double balloon catheter 100 of FIG. 1A. As mentioned, the lumens 101a and 102a are communicatively connected with the balloons 307b and 315b, respectively. Additionally, the lumens 105a and 108a are communicatively connected to the balloons 315a and 307a, respectively. The lumens 104a and 107a are integrally connected or suitably attached to the balloons 307a and 307b, which can contain the radioactive wires 113 and 115, or fluid or other therapeutic agent, for treatment. The lumen 104a can be integrally formed along or suitably attached to the inner wall 307w of the balloon 307a and the lumen 107a can be integrally formed along or suitably attached to an inner wall 307z of the balloon 307b, for example. The central lumen 109a runs along the central portion 180 of the dual double balloon catheter 100 and is communicatively connected to the tip 311 in the distal end portion 182 of the catheter 100 and is adapted to include the radioactive wire 119, or other therapeutic agent, for treatment.

Figure 1C:
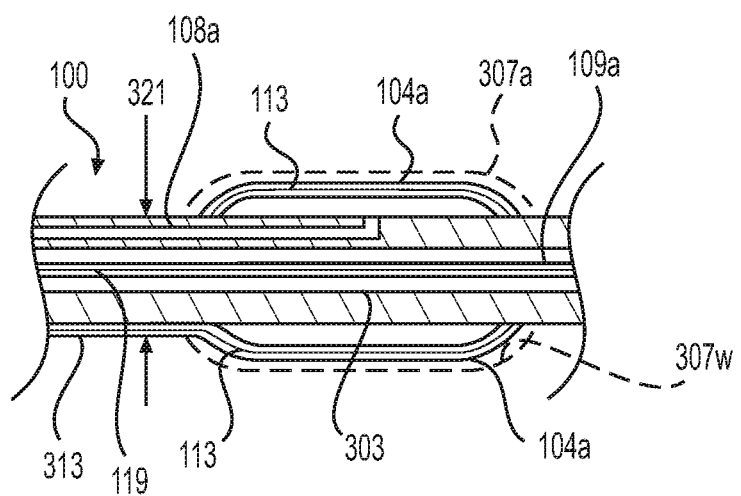
FIG. 1C is an enlarged detailed view showing the various lumens and connections of the dual double balloon catheter of FIG. 1A including a balloon with a radioactive wire in a lumen according to the present invention.

Referring now to FIG. 1C, FIG. 1C shows the enlarged view of the balloon 307a. The radioactive wire 113 passes inside the lumen 104a along a side of the balloon 307a. The lumen 108a is communicatively connected with the balloon 307a for inflating or deflating it to the desired size. The lumen 109a is positioned within the central main lumen 303, as indicated. A diameter 321 of the dual double balloon catheter 100 of FIG. 1A is typically about 0.45 cm. However, the diameter 321 can be of any suitable value depending on the use of the dual double balloon catheter 100 and is not to be construed in a limiting sense. Additionally, the dual-balloon inflators, such as pumps or syringes, as can be part of a multi-balloon inflator associated with the proximal end portion of the catheter, are respectively associated with the lumens 101a and 108a that selectively inflate the balloons 307a and 307b as can contain fluid, such as air or any other liquid for inflation of the balloons 307a and 307b. In some embodiments, the balloons 307a and 307b can contain contrast agents, such as for imaging, for example.

Figure 2A:
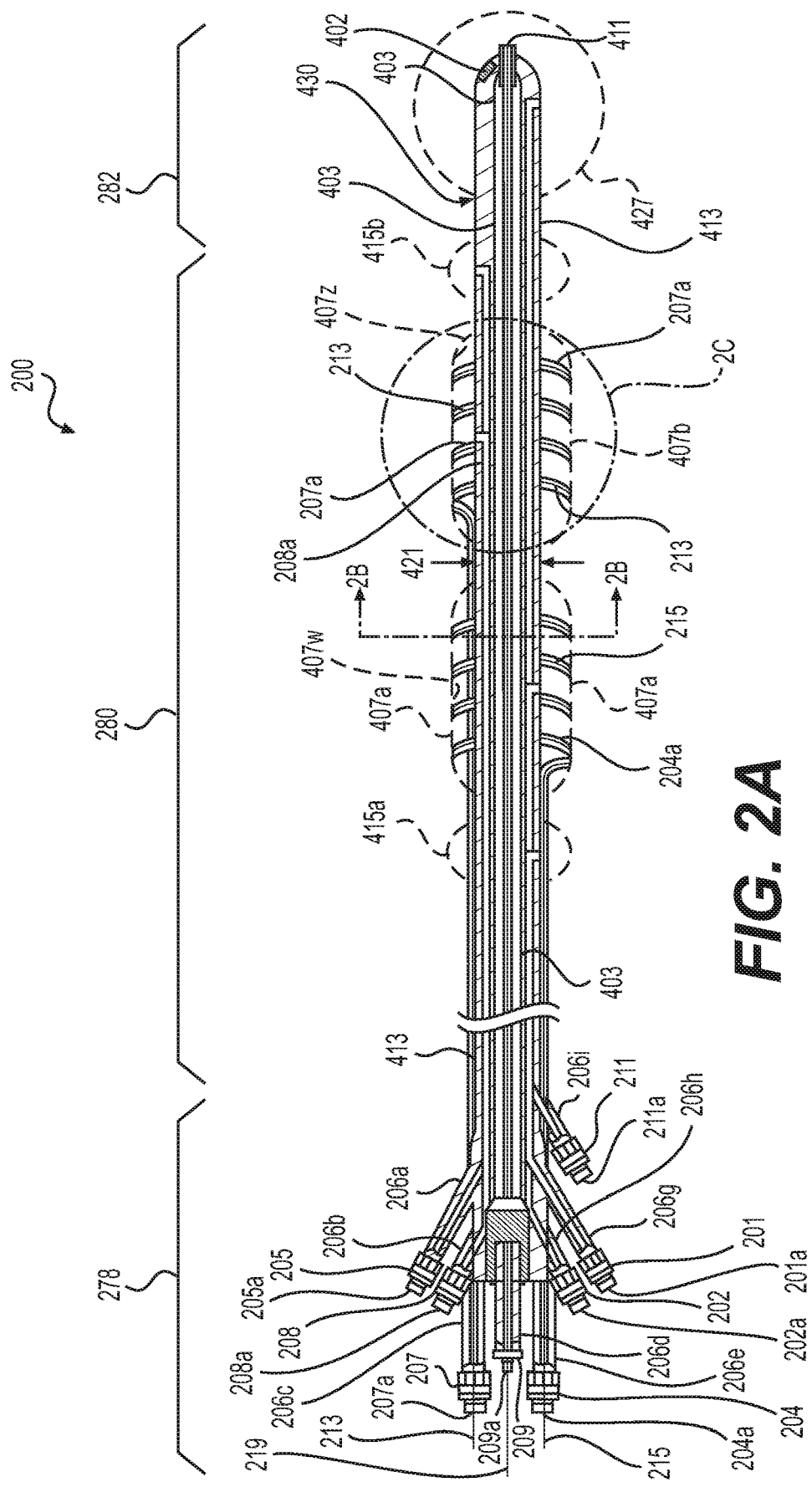
FIG. 2A is a longitudinal plan view of an embodiment of a dual double balloon catheter having balloons with a spiral lumen, which may include a radioactive wire inside a spiral lumen, according to the present invention.

There is illustrated in FIG. 2A an exemplary embodiment of a dual double balloon catheter 200 constructed according to the teachings of the invention. The dual double balloon catheter 200 includes a proximal end portion 278 having a plurality of connectors or locking mechanisms, such as luer-locks, a central portion 280, such as having a tubular body 413, and a distal end portion 282 having a marker 402, such as an X-ray positioning marker, and a tip 411 that can provide or include an extraction opening that can be used for drawing human fluid material such as urine, semen, pus, blood, fat cells, malignant tissue, etc. from a cavity for or in conjunction with a treatment. The tip 411 can include or provide in association with the extraction opening of the tip 411 an inner seal that allows for a single direction of flow for removal of fluid or material from the cavity.

The dual double balloon catheter 200 is designed for multiple uses and features as, for example, to deliver radiation or other therapeutic agent to bodily or surgically created cavities or organs, such as the esophageal and stomach areas having abnormal cancerous growth and tumors, while at a same time or at different times removing human material, such as fluid liquid, e.g., blood, urine, fat and tissue, in conjunction with a treatment, if desired.

The dual double balloon catheter 200 has a plurality of male or female luer-lock connections for selectively introducing into lumens of the catheter treatment or inflation mediums. For example, a luer-lock connection 211 having a lumen 211a associated with a neck portion 206i of the catheter 200 as can deliver an inflation medium through the lumen 211a to selectively inflate a secondary treatment balloon 427 positioned at the distal end portion 282 of the catheter 200. A luer-lock connection 201 having a lumen 201a associated with a neck portion 206g as can deliver an inflation medium through the lumen 201a to selectively inflate the balloon 415a. A luer-lock connection 202 having a lumen 202a associated with a neck portion 206h of the catheter 200 can deliver an inflation medium through the lumen 202a to selectively inflate the balloon 407a.

A luer-lock connection 204 having a lumen 204a associated with a neck portion 206e of the catheter 200 can be adapted to include in the lumen 204a a radioactive wire 215 or other therapeutic agent inside it as can be inserted inside the lumen 204a for radiation or other therapeutic treatment associated with the balloon 407a. The lumen 204a can be integrally formed along or suitably attached to an inner wall 407w of the balloon 407a, for example. A luer lock connection 209 having a lumen 209a associated with a neck portion 206d can be adapted to include in the lumen 209a a radioactive wire 219 as can be inserted inside the lumen 209a for radiation treatment, such as within the balloon 427 located at the tip 411 of the catheter 200, or the lumen 209a, when not associated with a balloon, can be used to remove, such as by suction, fluids or other material from a cavity, for example.

A luer-lock connection 207 having a lumen 207a associated with a neck portion 206c of the catheter can be adapted to include a radioactive wire 213 or other therapeutic agent as can be inserted inside the lumen 207a for radiation or other therapeutic treatment associated with a balloon 407b. The lumen 207a can be integrally formed along or suitably attached to an inner wall 407z of the balloon 407b, for example. A luer-lock connection 208 having a lumen 208a associated with a neck portion 206b of the catheter 200 can deliver an inflation medium through the lumen 208a to selectively inflate the balloon 407b. A luer-lock connection 205 having a lumen 205a associated with a neck portion 206a of the catheter 200 can deliver an inflation medium through the lumen 205a to selectively inflate a balloon 415b.

Figure 2B:
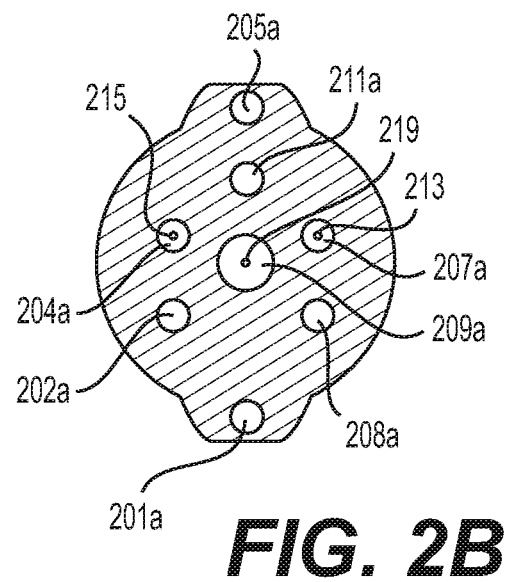
FIG. 2B is a cross-sectional view taken along lines 2B-2B of FIG. 2A showing the various lumens of the dual double balloon catheter of FIG. 2A according to the present invention.

FIG. 2B shows the cross sectional view along the 2B-2B plane of the catheter 200 of FIG. 2A. The peripheral lumens 201a and 211a are communicatively connected with the balloons 415a and 427, respectively. Additionally, the peripheral lumens lumen 205a and 208a are communicatively connected to the balloons 415b and 407b, respectively. The peripheral lumens 204a and 207a are integrally connected to or suitably attached to the balloons 407a and 407b, which can contain the radioactive wire or fluid or other therapeutic agent for treatment. The peripheral lumen 202a is communicatively connected to the balloon 407a. The central lumen 209a runs along the central portion 280 of the catheter 200 in a central main lumen 403 and is communicatively connected to the tip 411.

Figure 2C:
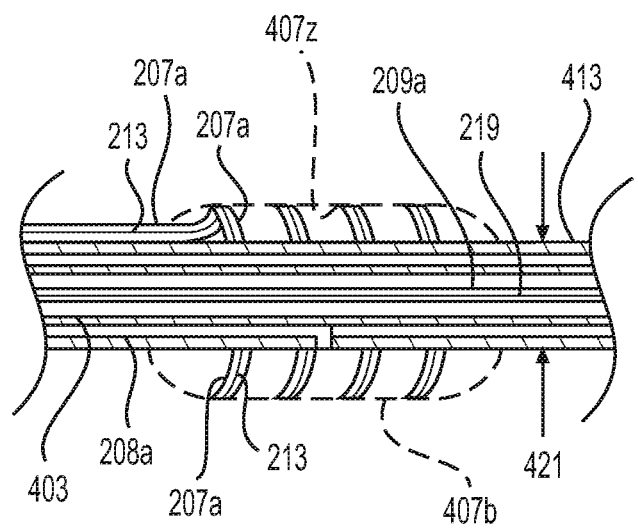
FIG. 2C is an enlarged detailed view of a side balloon having a spiral lumen with a radioactive wire inside a spiral lumen, of the dual double balloon catheter of FIG. 2A according to the present invention.

FIG. 2C shows an enlarged view of the balloon 407b of the catheter 200 of FIG. 2A. The radioactive wire 213 passes inside the lumen 207a along the side of the balloon 407b in a generally spiral pattern or configuration. The lumen 208a is communicatively connected with the balloon 407b for selectively inflating and deflating it to the desired size by a suitable inflation medium. The central main lumen 403 is indicated having the lumen 209a positioned within, as indicated. The diameter 421 of the catheter 200 of FIG. 2A is typically 0.45 cm. However, the diameter 421 can be of any suitable value depending on the use of the catheter 200 and is not to be construed in a limiting sense.

Figure 3A:
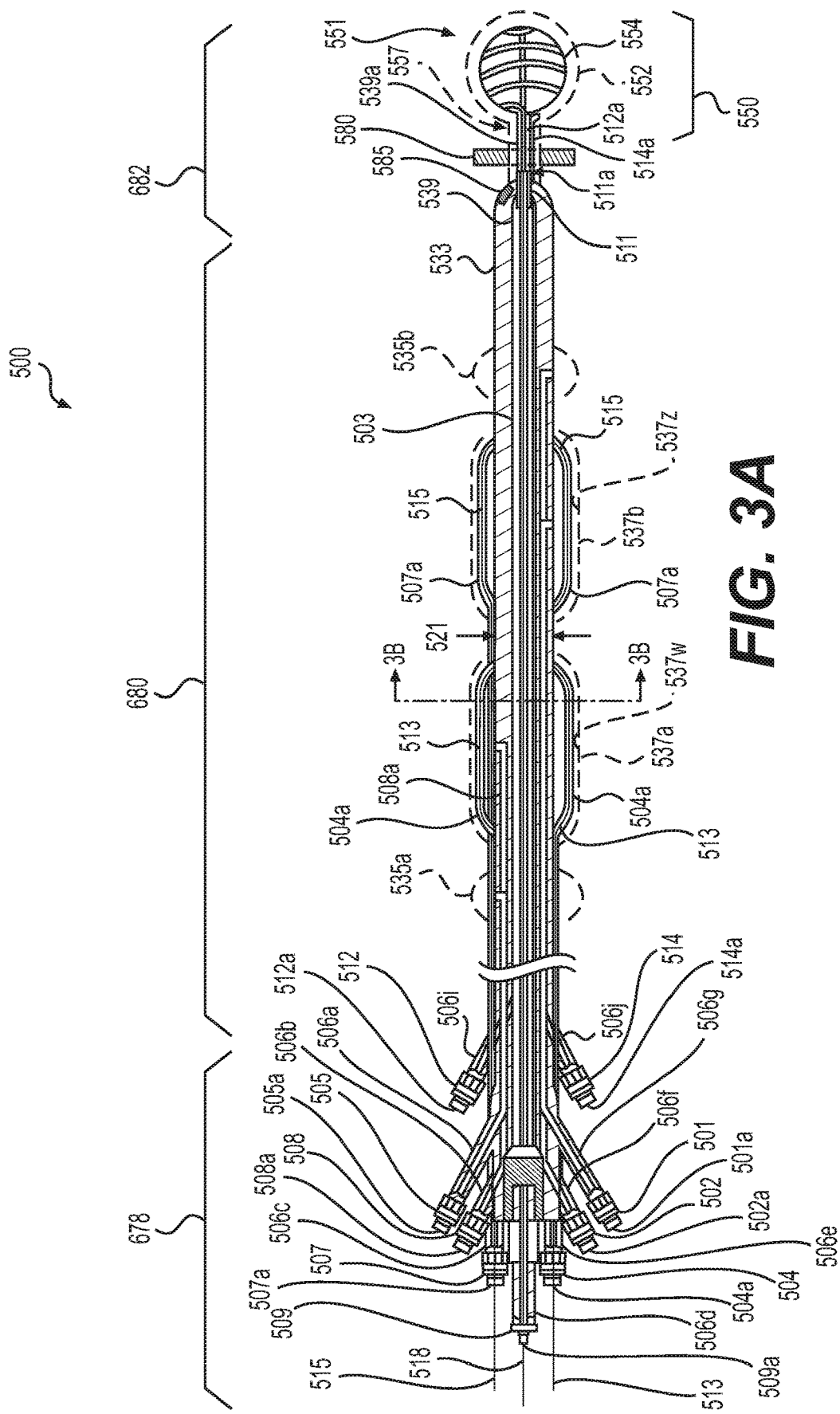
FIG. 3A is a longitudinal plan view of an embodiment of a dual double balloon catheter having a secondary treatment balloon at the distal end portion of the catheter fitted with a connector or locking mechanism, such as a luer-lock mechanism, according to the present invention.

Referring now to FIG. 3A, there is illustrated an embodiment of an exemplary dual double balloon catheter 500 constructed according to the teachings of the invention. The catheter 500 includes a proximal end portion 678 having a plurality of luer-locks, a central portion 680 including a tubular body 533 and a distal end portion 682 having positioned thereon a secondary treatment balloon 551 having one or more of a spiral lumen or a longitudinal lumen containing a corresponding radioactive treatment wire or other therapeutic agent.

The dual double balloon catheter 500 and its associated components are similar in construction to the catheter 100 of FIG. 1A, such as in relation to the structure and arrangement of the corresponding balloons and corresponding lumens, but includes the addition of a secondary treatment balloon assembly 550 including a secondary treatment balloon 551. The catheter 500 can include a marker 585, such as an x-ray marker, located in the area of a tip 511 of the catheter 500 located in the distal end portion 682 thereof to indicate a location of the catheter 500, and more particularly, a location of the distal end portion 682 of the catheter 500, for example, the tip 511 can also provide or include an extraction opening to enable removal or fluid or material from a cavity which the catheter is positioned in the cavity for a treatment. The tip 511 can include or provide in association with the extraction opening of the tip 511 an inner seal that allows for a single direction of flow for removal of fluid or material from the cavity. The balloons of the catheter 500 can contain fluid, such as air or any other liquid, for inflation of the balloon. In some embodiments, the balloons of the catheter 500 can contain contrast agents for imaging, for example.

The dual double balloon catheter 500 of FIG. 3A can have various multiple uses and features, for example, to deliver radiation to the esophageal and stomach areas having abnormal cancerous growth and tumors, while at a same time or at different times can remove material, such as human fluid liquid, e.g., blood, urine, pus, fat and tissue, as part of or in conjunction with a treatment, if desired.

The dual double balloon catheter 500 has suitable connectors or locking mechanisms, such as can be male or female luer-lock connections, for example. The catheter 500 of FIG. 3A additionally includes the secondary treatment balloon assembly 550 including the secondary treatment balloon 551 to treat the stomach area with higher doses of radiation and to target certain tumors, which will be described in greater detail in relation to FIG. 3C.

In the catheter 500, for example, a luer-lock connection 514 having lumen 514a a neck portion 506j of the catheter 500 is adapted to selectively inflate and deflate an outer secondary treatment balloon 552 of the secondary treatment balloon 551. A luer-lock connection 512 having a lumen 512a associated with a neck portion 506i of the catheter 500 is adapted to selectively inflate and deflate an inner secondary treatment balloon 554 of the secondary treatment balloon 551. A luer-lock connection 501 having a lumen 501a associated with a neck portion 506g of the catheter 500 is adapted to selectively inflate and deflate a balloon 537b.

A luer-lock connection 502 having a lumen 502a associated with a neck portion 506f of the catheter 500 is adapted to selectively inflate and deflate a balloon 535b. A luer lock connection 504 having a lumen 504a associated with a neck portion 506e of the catheter 500 can be adapted to include in the lumen 504a a radioactive wire 513 or other therapeutic agent inside it as can be inserted inside the lumen 504a for radiation or other therapeutic treatment associated with a balloon 537a. The lumen 504a can be integrally formed along or suitably attached to an inner wall 537w of the balloon 537a, for example. A luer-lock connection 509 having a lumen 509a associated with a neck portion 506d can be adapted to include in the lumen 509a a radioactive wire 518 or other therapeutic agent inside it as can be inserted inside the lumen 509a for radiation or other therapeutic treatment associated with the secondary treatment balloon 551.

A luer-lock connection 507 having a lumen 507a associated with a neck portion 506c as can be adapted to include in the lumen 507a a radioactive wire 515 or other therapeutic agent inside it as can be inserted inside the lumen 507a for radiation or other therapeutic treatment associated with the treatment balloon 537b. The lumen 507a can be integrally formed along or suitably attached to an inner wall 537z of the balloon 537b, for example. A luer-lock connection 508 having a lumen 508a associated with a neck portion 506b of the catheter 500 is adapted to selectively inflate the balloon 537a. A luer-lock connection 505 having a lumen 505a associated with a neck portion 506a of the catheter 500 is adapted to selectively inflate and deflate the balloon 535a. The central lumen 509a can extend through the tip 511 of the catheter 500 to the inner secondary treatment balloon 554.

Figure 3B:
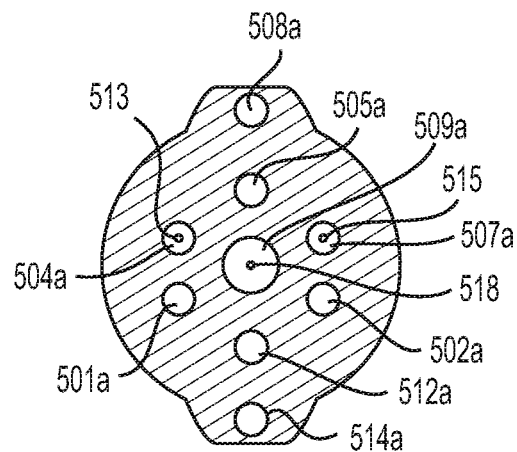
FIG. 3B is a cross-sectional view taken along lines 3B-3B of FIG. 3A showing the various lumens of the dual double balloon catheter of FIG. 3A according to the present invention.

FIG. 3B shows the cross sectional view along the 3B-3B plane of the catheter 500 of FIG. 3A to illustrate an arrangement of the lumens 501a, 502a, 504a, 505a, 507a, 508a, 509a, 512a and 514a. The peripheral lumens 501a and 502a are communicatively connected with the balloons 537b and 535b, respectively. Additionally, the peripheral lumens 505a and 508a are communicatively connected to the balloons 535a and 537a, respectively. The peripheral lumens 504a and 507a are integrally connected to or suitably attached to the balloons 537a and 537b, respectively, which run along the inner walls thereof and which can contain the radioactive wires 513 and 515 or a radioactive fluid or a radioactive material for a treatment. The central lumen 509a runs along the central portion 680 of the catheter 500 within a central main lumen 539 and is communicatively connected to the tip 511. The peripheral lumens 514a and 512a are respectively communicatively connected to the outer secondary treatment balloon 552 and the inner secondary treatment balloon 554 of the secondary treatment balloon 551 to respectively inflate and deflate these balloons with a fluid medium.

Figure 3C:
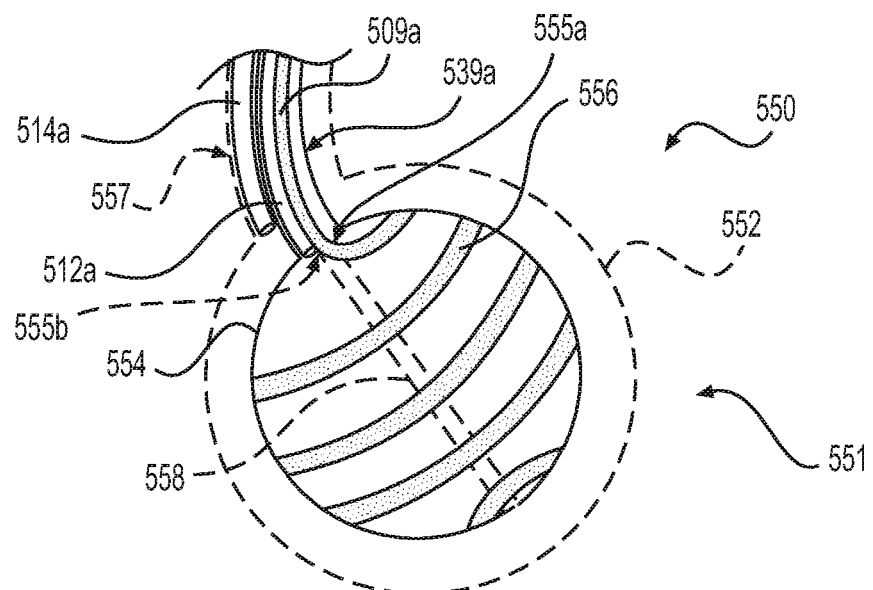
FIG. 3C is a detailed view of the secondary treatment balloon of the dual double balloon catheter of FIG. 3A at the distal end portion of the catheter having a spiral lumen with a radioactive wire, and indicating a second treatment lumen, according to the present invention.

Referring now to FIG. 3C, there is shown an enlarged view of the secondary treatment balloon assembly 550 including the secondary treatment balloon 551 including the outer secondary treatment balloon 552 and the inner secondary treatment balloon 554. The outer secondary treatment balloon 552 and the inner secondary treatment balloon 554 can contain fluid, such as air or any other suitable liquid, for inflation of the balloon. In some embodiments, the outer secondary treatment balloon 552 and the inner secondary treatment balloon 554 can contain contrast agents for imaging, for example. The radioactive wire or radioactive fluid can pass around the spiral or longitudinal shaped lumens of the secondary treatment balloon 551 for delivering the radiation or other therapeutic agent for a treatment at the chosen site.

Referring to FIGS. 3A and 3C, in the embodiment of the catheter 500, the secondary treatment balloon assembly 550 can be integrally formed with or affixed to or otherwise positioned in conjunction with the catheter 500, such as by a suitable glue or adhesive, for example, as indicated at an attachment area 511a. The secondary treatment balloon assembly 550 includes the secondary treatment balloon 551 that includes the outer secondary treatment balloon 552 and the inner secondary treatment balloon 554.

The outer secondary treatment balloon 552 and the inner secondary treatment balloon 554 can be selectively inflated and deflated to be positioned in a body cavity or a surgically created cavity to be treated, for example. The lumen 512a communicatively connects with the inner secondary treatment balloon 554 and the lumen 514a communicatively connects with the outer secondary treatment balloon 552 to respectively selectively inflate and deflate the inner secondary treatment balloon 554 and the outer secondary treatment balloon 552 to position and/or stabilize the secondary treatment balloon 551 in a body cavity or surgically created cavity to be treated. Similarly, the lumens 512a and 514a can receive a fluid medium, as previously described, such as saline solution or a gaseous medium, such as by a syringe or other suitable delivery mechanism, such as a pump, to selectively inflate and deflate the inner secondary treatment balloon 554 and the outer secondary treatment balloon 552, to provide a corresponding balloon shape, size and configuration in the body cavity for the treatment, for example.

The secondary treatment balloon 551 has at least one or both of a first secondary treatment lumen 556 and a second secondary treatment lumen 558, the second secondary treatment lumen 558 being optionally indicated in FIG. 3C by dashed lines. The first secondary treatment lumen 556 can be integrally formed with or affixed to or otherwise positioned in conjunction with the inner secondary treatment balloon 554, such as by a suitable glue or adhesive, for example. The first secondary treatment lumen 556 is desirably of a generally spiral type configuration, for example, as illustrated in FIGS. 3A and 3C. The first secondary treatment lumen 556 can be positioned either on an interior surface or on an exterior surface of the inner secondary treatment balloon 554, for example, but desirably is placed on an interior surface portion thereof.

The first secondary treatment lumen 556 is communicatively connected to the central lumen 509a by a connector or connector portion 539a and by a connector 555a, as can extend into a neck area 557 of the secondary treatment balloon assembly 550, or can be integrally formed therewith, to deliver a radioactive dose or other therapeutic treatment agent through the central lumen 509a, through the connector or connector portions 539a, 555a and through the first secondary treatment lumen 556 to a treatment site in a cavity, such as by insertion of the radioactive wire 518 or providing a therapeutic agent through the central lumen 509a, the connectors 539a and 555a and the first secondary treatment lumen 556, for example.

In the inner secondary treatment balloon 554, the second secondary treatment lumen 558 can be integrally formed with or affixed to or otherwise positioned in conjunction with the inner secondary treatment balloon 554, such as by a suitable glue or adhesive, for example. The second secondary treatment lumen 558 is communicatively connected to the central lumen 509a by the connector or connector portion 539a and by a connector 555b to deliver a radioactive dose or other therapeutic treatment through the central lumen 509a, through the connector or connector portions 539a, 555b to a treatment site in a cavity, such as by insertion of the radioactive wire 518 or providing a therapeutic agent through the central lumen 509a, the connectors or connector portions 539a, 555b and through the second secondary treatment lumen 558, for example.

As discussed, the second secondary treatment lumen 558 is communicatively connected to the central lumen 509a by the connector or connector portions 539a, 555b, and can also be integrally formed therewith, to deliver a radioactive dose or other therapeutic treatment agent through the central lumen 509a, the connectors or connector portions 539a, 555b and through the second secondary treatment lumen 558 to a treatment site in a cavity, such as by insertion of the radioactive wire 518 or providing a therapeutic agent through the central lumen 509a, the connectors or connector portions 539a, 555b and the second secondary treatment lumen 558, for example. The second secondary treatment lumen 558 is desirably formed in an interior portion of the inner secondary treatment balloon 554 desirably extending in a generally longitudinal direction in a generally central portion of the inner secondary treatment balloon 554, for example.

Continuing with reference to FIGS. 3A and 3C, in the secondary treatment balloon assembly 550 there can be included a connector or locking mechanism 580, such as a suitable luer lock, that can include suitable male or female connectors to selectively connect the secondary treatment balloon assembly 550 to the catheter 500 in the attachment area 511a. The connector or locking mechanism 580 or a portion thereof can be integrally formed with or suitably connected with the distal end portion 682 of the catheter 500 at the attachment area 511a, such as with a suitable glue or adhesive, for example. Also, the connector or locking mechanism 580 or a portion thereof can be integrally formed with or suitably connected with the proximal end of the neck area 557 of the secondary treatment balloon assembly 550, such as with a suitable glue or adhesive. Such connector or locking mechanism 580 can assist in enabling attaching or exchanging with the catheter 500 various sizes and configurations of the secondary treatment balloon assembly 550 to facilitate treatment and treatment options, for example.

Also, in the secondary balloon assembly 550, the lumens 509a, 512a and 514a can also be extended through the neck area 557 by one or more a suitable connector lumens, as can be integrally formed or joined therewith by a suitable process or method, to respectively communicate with the inner secondary treatment balloon 554, the outer secondary treatment balloon 552, the first secondary treatment lumen 556 and the second secondary treatment lumen 558, as described.

In various embodiments, the catheters, such as the catheters 100, 200 and 500, as described, can be made of a polymeric material, such as polyurethane, polyethylene, polymethyl methacrylate (PMMA), polycarbonate, styrenic block copolymers, polybutylene terephthalate (PBT), Teflon, Nylon, PVC, etc., or other suitable materials. The balloons of embodiments of catheters, such as of the catheters 100, 200 and 500, can be made of nylon, polyurethane, Polyether block amide Pebax®, poly(ethylene terephthalate), commonly abbreviated PET or other thermoplastic elastomers or other suitable materials, for example.

While various embodiments of inflatable balloons of embodiments of the multi-purpose balloon catheters described herein have been associated with a single circular treatment lumen or a single treatment lumen, or associated with first and second treatment lumens, positioned in association with a distal inflatable balloon of the catheter, embodiments of distal inflatable balloons for delivery of treatment should not be construed as so limited. In this regard, a distal inflatable balloon for treatment can include a relatively large number of treatment lumens associated with a corresponding distal inflatable balloon, such as can include one to fifteen treatment lumens associated with or attached to a distal inflatable balloon, desirably attached to or associated with an inner wall or inner surface of the balloon or attached to or associated with an inner balloon of a distal inflatable balloon, for example.

Such multiple treatment lumens associated with a distal treatment balloon can be selectively used for delivery of a plurality of treatments, procedures, or other therapeutic purposes, such as for delivery of radiation therapy, delivery of contrast agents for imaging or mapping a location, delivery of various therapeutic agents, etc. for example, using a single distal balloon associated with a catheter, similar to those described herein. For example, a distal inflatable balloon associated with a catheter for treatment or a related procedure desirably can include five such treatment lumens, such as one treatment lumen being positioned at a center of an inner treatment balloon and four treatment lumens positioned in association with the periphery of the inner treatment balloon, such as of the distal inflatable balloon, for example.

Also, in various catheter embodiments, one or more of the balloons of the catheters can be uncoated or coated with a lubricant for lubrication for ease of insertion or for antimicrobial properties. Also, in various catheter embodiments, various therapeutic drugs or therapeutic agents can be coated onto or formed into the surface of one or more of the balloons and/or all or a part of the catheter body for releasing drug(s) or therapeutic agent(s) internally to a specific location of the cavity for or in conjunction with a treatment.

It is to be understood that the present invention is not limited to the embodiments described above, but encompasses any and all embodiments within the scope of the following claims.

I claim:

1. A multi-balloon catheter, comprising:
   the catheter having a proximal end portion, a central portion and a non-branching distal end portion;
   a plurality of lumens positioned in association with the catheter extending from the proximal end portion of the catheter;
   a central main lumen extending coaxially along the central portion towards the distal end portion;
   one of the plurality of lumens being a central lumen coaxially disposed within the central main lumen and extending from the proximal end portion to the distal end portion;
   a plurality of inflatable balloons positioned in association with the central portion of the catheter, the plurality of inflatable balloons being in communication with respective ones of at least the remainder of the plurality of lumens and configured to enable filling the plurality of inflatable balloons with an inflation medium to enable selectively inflating and deflating at least one of the plurality of inflatable balloons independently of at least one of the remainder of the plurality of inflatable balloons to selectively position and/or stabilize the catheter in a cavity for a treatment, at least one of the plurality of inflatable balloons including at least one corresponding lumen of the plurality of lumens configured to respectively receive a treatment medium or a contrast medium for the treatment, each of the plurality of inflatable balloons being spaced in a longitudinal direction along a length of the catheter in a non-overlapping contiguous arrangement on a common longitudinal axis of the catheter; and a secondary treatment balloon communicatively associated with the distal end portion of the catheter via a connector and being in communication with the central lumen, the central lumen being configured to receive and selectively provide the secondary treatment balloon with at least one of the treatment medium or the contrast medium for the treatment, wherein the distal end portion of the catheter has a tip at a distal end, the secondary treatment balloon surrounding the tip or disposed past the tip, wherein the central lumen extends through the tip of the catheter to the secondary treatment balloon via the connector to deliver the at least one of the treatment medium or the contrast medium through the central lumen and through the connector to the secondary treatment balloon for the treatment, and wherein the secondary treatment balloon comprises one or more of at least one first secondary treatment lumen and at least one second secondary treatment lumen to facilitate delivery of the at least one of the treatment medium or the contrast medium, and the at least one second secondary treatment lumen extends generally longitudinally into the secondary treatment balloon.

2. The multi-balloon catheter according to claim 1, wherein:
each first secondary treatment lumen is positioned in association with a periphery of the secondary treatment balloon, each first secondary treatment lumen is respectively communicatively connected with the central lumen and is configured to receive and selectively provide the secondary treatment balloon with the at least one of the treatment medium or the contrast medium for the treatment, and
each second secondary treatment lumen is positioned in an interior central portion of the secondary treatment balloon, each second secondary treatment lumen is respectively communicatively connected with the central lumen and is configured to receive and selectively provide the secondary treatment balloon with the at least one of the treatment medium or the contrast medium for the treatment.

3. The multi-balloon catheter according to claim 2, wherein:
the at least one said first secondary treatment lumen has a generally spiral configuration.

4. The multi-balloon catheter according to claim 1, wherein the secondary treatment balloon comprises:
an outer secondary treatment balloon being in communication with at least one of the remainder of the plurality of lumens to enable selective inflation or deflation of the outer secondary treatment balloon and facilitate selective positioning and/or stabilizing of the secondary treatment balloon for the treatment; and
an inner secondary treatment balloon being in communication with at least one of the remainder of the plurality of lumens and the central lumen and being configured to receive and selectively provide the inner secondary treatment balloon with at least one of the treatment medium or the contrast medium for the treatment or enable selective inflation or deflation of the inner secondary treatment balloon for the treatment.

5. The multi-balloon catheter according to claim 4, wherein:
each first secondary treatment lumen is positioned in association with a periphery of the inner secondary treatment balloon, each first secondary treatment lumen is respectively communicatively connected with the central lumen and is configured to receive and selectively provide the inner secondary treatment balloon with the at least one of the treatment medium or the contrast medium for the treatment, and
each second secondary treatment lumen is positioned in an interior central portion of the inner secondary treatment balloon, each second secondary treatment lumen is respectively communicatively connected with the central lumen and is configured to receive and selectively provide the inner secondary treatment balloon with the at least one of the treatment medium or the contrast medium for the treatment.

6. The multi-balloon catheter according to claim 5, wherein:
the at least one said first secondary treatment lumen has a generally spiral configuration.

7. The multi-balloon catheter according to claim 1, wherein:
the treatment medium comprises a radioactive material.

8. The multi-balloon catheter according to claim 7, wherein:
the radioactive material comprises a radioactive wire, a radioactive seed or a radioactive isotope in a medium.

9. The multi-balloon catheter according to claim 8, wherein:
the radioactive wire or the radioactive seed comprises a material selected from the group consisting of Ir-192, Au-198, I-125, Yb-168, Sr-90 and Cs-131.

10. The multi-balloon catheter according to claim 9, wherein:
the radioactive wire or the radioactive seed delivers a dose of radiation from 1 Curie to 10 Curies.

11. The multi-balloon catheter according to claim 1, wherein:
the cavity for the treatment is a body cavity or a surgically created cavity.

12. The multi-balloon catheter of claim 1, wherein:
the multi-balloon catheter is configured to enable delivering a radiation treatment to a stomach area.

13. The multi-balloon catheter of claim 1, wherein:
the catheter comprises a polymeric material selected from the group consisting of polyurethane, polyethylene, polymethyl methacrylate (PMMA), polycarbonate, styrenic block copolymers, polybutylene terephthalate (PBT), Teflon, Nylon or PVC.

14. The multi-balloon catheter of claim 1, wherein:
the plurality of inflatable balloons or the secondary treatment balloon comprise a material selected from the group consisting of nylon, polyurethane, polyether block amide, polyethylene terephthalate or combinations thereof.

15. The multi-balloon catheter of claim 1, wherein:
at least one of the plurality of inflatable balloons, the secondary treatment balloon or at least a portion of the catheter are coated with a medicinal agent configured to enable releasing the medicinal agent internally to a site of a body cavity for or associated with the treatment.

16. A multi-balloon catheter, comprising:
the catheter having a proximal end portion, a central portion and a non-branching distal end portion;
a plurality of lumens associated with the catheter extending from the proximal end portion of the catheter;
a central main lumen extending coaxially along the central portion towards the distal end portion;
one of the plurality of lumens being a central lumen coaxially disposed within the central main lumen and extending from the proximal end portion to the distal end portion;
a plurality of inflatable balloons associated with the central portion of the catheter, the plurality of inflatable balloons each being configured to be filled with an inflation medium to enable selectively inflating and deflating of at least one of the plurality of inflatable balloons independently of at least one of the remainder of the plurality of inflatable balloons to selectively position and/or stabilize the catheter in a cavity for a treatment, at least one of the plurality of inflatable balloons further including at least one corresponding lumen of the plurality of lumens configured to respectively receive a treatment medium or a contrast medium for the treatment, each of the plurality of inflatable balloons being arranged in a longitudinal direction along a length of the catheter in a non-overlapping contiguous arrangement on a common longitudinal axis of the catheter;
a secondary treatment balloon communicatively associated with the distal end portion of the catheter via a connector and being in communication with the central lumen, the central lumen being configured to receive and selectively provide the secondary treatment balloon with at least one of the treatment medium or the contrast medium for the treatment,
wherein the distal end portion of the catheter has a tip at a distal end, the secondary treatment balloon surrounding the tip or disposed past the tip,
wherein the central lumen extends through the tip of the catheter to the secondary treatment balloon via the connector to deliver the at least one of the treatment medium or the contrast medium through the central lumen and through the connector to the secondary treatment balloon for the treatment,
wherein the secondary treatment balloon comprises one or more of at least one first secondary treatment lumen having a generally spiral configuration and at least one second secondary treatment lumen, the at least one second secondary treatment lumen extending generally longitudinally in an interior central portion of the secondary treatment balloon, each first secondary treatment lumen and each second secondary treatment lumen respectively communicating with a corresponding one of the plurality of lumens to facilitate delivery of the at least one of the treatment medium or the contrast medium; and
a multi-balloon inflator having a plurality of connectors respectively associated with the plurality of lumens, the plurality of connectors being configured to selectively inflate or deflate the plurality of inflatable balloons and the secondary treatment balloon and to selectively provide one or more of the plurality of inflatable balloons and the secondary treatment balloon with the treatment medium or the contrast medium for the treatment.

17. A treatment balloon for a catheter, comprising:
a secondary treatment balloon configured to be communicatively associated with a distal end portion of a catheter, the distal end portion of the catheter having a tip at a distal end, the secondary treatment balloon surrounding the tip or disposed past the tip, the secondary treatment balloon configured to be in communication with at least one corresponding lumen of one or more lumens associated with the catheter, the at least one corresponding lumen of the one or more lumens associated with the catheter being configured to respectively receive and selectively provide to the secondary treatment balloon at least one of a treatment medium or a contrast medium for a treatment or enable selective inflation or deflation of the secondary treatment balloon to selectively position and/or stabilize the secondary treatment balloon for the treatment;
at least one secondary treatment lumen positioned in association with the secondary treatment balloon, each secondary treatment lumen configured to be respectively communicatively connected with a respective said corresponding lumen of the one or more lumens associated with the catheter and being configured to respectively receive and selectively provide the secondary treatment balloon with at least one of the treatment medium or the contrast medium for the treatment;
a connector for selectively connecting the secondary treatment balloon to the catheter to deliver the at least one of the treatment medium or the contrast medium through the connector to the secondary treatment balloon for the treatment;
wherein the secondary treatment balloon comprises:
an outer secondary treatment balloon; and
an inner secondary treatment balloon;
wherein the at least one secondary treatment lumen comprises:
at least one first secondary treatment lumen having a generally spiral configuration; and
at least one second secondary treatment lumen extending generally longitudinally into the secondary treatment balloon;
wherein each first secondary treatment lumen is positioned in association with a periphery of the inner secondary treatment balloon, each first secondary treatment lumen is configured to be respectively communicatively connected with at least one respective said corresponding lumen of the one or more lumens associated with the catheter and is configured to receive and selectively provide the inner secondary treatment balloon with the at least one of the treatment medium or the contrast medium for the treatment; and
wherein each second secondary treatment lumen is positioned inside the inner secondary treatment balloon, each second secondary treatment lumen is configured to be respectively communicatively connected with at least one respective said corresponding lumen of the one or more lumens associated with the catheter and is configured to receive and selectively provide the inner secondary treatment balloon with the at least one of the treatment medium or the contrast medium for the treatment.

18. The treatment balloon for the catheter according to claim 17, wherein:
the at least one said second secondary treatment lumen extends generally longitudinally in an interior central portion of the inner secondary treatment balloon.

19. The treatment balloon for the catheter according to claim 17, wherein:
the outer secondary treatment balloon is configured to be in communication with at least one respective said corresponding lumen of the one or more lumens associated with the catheter to enable selective inflation or deflation of the outer secondary treatment balloon and facilitate selective positioning and/or stabilizing of the secondary treatment balloon for the treatment, and the inner secondary treatment balloon is configured to be in communication with at least one respective said corresponding lumen of the one or more lumens associated with the catheter to respectively receive and selectively provide the inner secondary treatment balloon with at least one of the treatment medium or the contrast medium for the treatment or enable selective inflation or deflation of the inner secondary treatment balloon for the treatment.

\* \* \* \* \*